United States Patent [19]

Fayter, Jr. et al.

[11] 4,399,076
[45] Aug. 16, 1983

[54] 1,1-DISUBSTITUTED 2-VINYL- AND 2-ETHYLCYCLOPROPANES

[75] Inventors: Richard G. Fayter, Jr., Fairfield; Allen L. Hall, Amelia, both of Ohio

[73] Assignee: National Distillers and Chemical Corporation, New York, N.Y.

[21] Appl. No.: 350,669

[22] Filed: Feb. 22, 1982

[51] Int. Cl.$^3$ .................. C07C 121/75; C07C 87/28; C07C 125/063; C07C 127/17
[52] U.S. Cl. .......................... 260/465 F; 260/465 R; 260/465 G; 260/465 K; 560/21; 560/27; 564/48; 564/50; 564/52; 564/53; 564/54; 564/56; 564/282; 564/284; 564/285; 564/288; 564/289; 564/338; 564/339
[58] Field of Search ........... 260/465 R, 465 K, 465 F, 260/465 G; 564/282, 288, 338, 48, 50, 52, 53, 54, 56, 284, 285, 289, 339; 560/27, 21

[56] References Cited

U.S. PATENT DOCUMENTS 4,252,739  2/1981  Fayter, Jr. et al. ............. 560/102 X

*Primary Examiner*—Dolph H. Torrence
*Attorney, Agent, or Firm*—Kenneth D. Tremain; Gerald A. Baracka

[57] ABSTRACT

2-Vinyl- and 2-ethylcyclopropanes having an aryl group and a nitrogen-containing radical substituted at the 1-position on the ring are provided. The novel 1,1-disubstituted 2-vinylcyclopropane and 2-ethylcyclopropane compounds of this invention have utility in herbicidal applications and are useful reactants. The 2-vinylcyclopropane derivatives are useful monomers for anionic and radical polymerizations.

8 Claims, No Drawings

1,1-DISUBSTITUTED 2-VINYL- AND 2-ETHYLCYCLOPROPANES

BACKGROUND OF THE INVENTION

1. Field of the Invention

This invention relates to novel 1,1-disubstituted 2-vinyl- and 2-ethylcyclopropane compounds. More particularly, the cyclopropane compounds have an aryl group and a nitrogen-containing radical, such as nitrile, amine, quaternary amine or the like, substituted at the 1-position on the ring and are useful as herbicides.

2. Discussion of the Prior Art

Cyclopropane derivatives having a nitrile or other nitrogen-containing radical substituted on the ring are known. For example, nitrile-substituted cyclopropanes have been reported by Kierstead et al. (*J. Chem. Soc.*, 1953, 1799–1803), Dehmlow (Angew, Chem. *Internat. Edit.*, Vol. 13, No. 3, 170–179(1974)) and I. Cho et al. (*Journal of Polymer Science*, Vol. 17, 3169–3182 1979; Vol. 17, 3183–3191 (1979); Vol. 18, 3053–3057(1980); and Polymers Letters Edition, Vol. 18(9), 639–642(1980)). Also, cyclopropanecarboxanilides are disclosed in U.S. Pat. No. 4,199,347. While some of the compounds reported in the above references have other groups substituted on the ring, and in some cases present at the same position on the ring as the nitrile or nitrogen-containing radical, none of the compounds have an aryl group present with a nitrile or other nitrogen-containing radical on the same ring carbon atom.

In U.S. Pat. No. 4,196,120 a cyclopropane compound of the formula

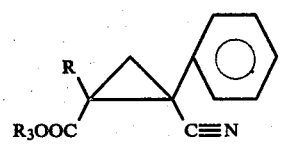

where R and $R_3$ are hydrogen or an alkyl group is employed to obtain an azabicyclohexan-2-one. While a nitrile and aryl group are substituted at the 1-position of the ring, a carboxylate group is necessarily present at the 2-position.

In view of the well established utility of compounds having the 2-vinylcyclopropane structure (e.g. the pyrethrins), it would be advantageous if compounds of the type disclosed in U.S. Pat. No. 4,196,120, i.e. 1,1-disubstituted with nitrile or related nitrogen-containing radical and an aryl group, were available.

SUMMARY OF THE INVENTION

We have now prepared novel 2-vinylcyclopropane compounds which are disubstituted at the 1-position with an aryl group and a nitrile or other nitrogen-containing radical, such as amine, quaternary amine, carbamyl, substituted and unsubstituted urea, and the like. In addition to the 2-vinylcyclopropane compounds, the corresponding 2-ethylcyclopropanes can be readily obtained by reducing the vinyl group. The compounds of this invention are useful as reactive intermediates and undergo radical or anionic polymerization, however, they are primarily useful as herbicides and in related applications.

The novel 1,1-disubstituted 2-vinyl- and 2-ethylcyclopropanes of this invention correspond to the formula

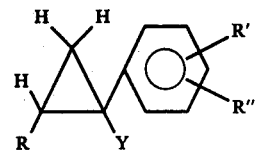

where R is an ethyl or vinyl group, R' and R" are, independently, selected from hydrogen, alkyl, halogen, nitro, cycloalkyl, aryl, hydroxyalkyl, alkoxyl and the like and Y is nitrile (—C≡N); an amine group of the formula

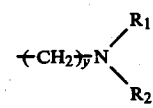

where y is an integer from 0 to 6 and $R_1$ and $R_2$ are hydrogen, alkyl, hydroxyalkyl, aryl, carboalkoxy or carbamyl; or a quaternary amine of the formula

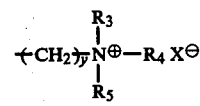

where y is an integer from 0 to 6, $R_3$, $R_4$ and $R_5$ are alkyl, aryl or hydroxyalkyl and X is an anion such as halide, hydroxide, sulfate, nitrate, alkylsulfate, alkylphosphate, fluoroborate and the like.

Particularly useful cyclopropane compounds have the formulae

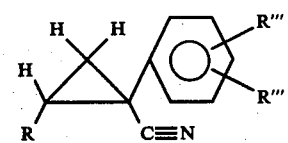

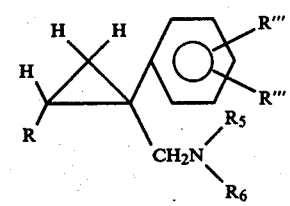

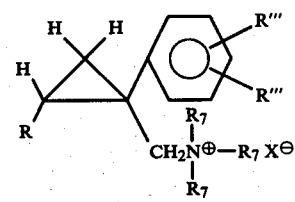

-continued

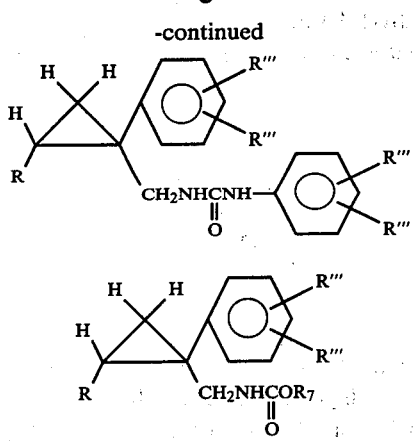

where R and X are the same as defined above, R''' is hydrogen, halogen, nitro, a $C_{1-4}$ alkyl, $C_{1-4}$ hydroxyalkyl or $C_{1-4}$ alkoxyl, $R_6$ is hydrogen or a $C_{1-8}$ alkyl and $R_7$ is $C_{1-8}$ alkyl.

DETAILED DESCRIPTION 1,1-Disubstituted 2-vinyl- and 2-ethylcyclopropanes have been prepared and correspond to the formula

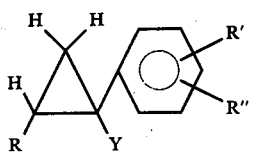

where R is an ethyl or vinyl group, R' and R'' are, independently, selected from hydrogen, halogen, nitro, alkyl, cycloalkyl, aryl, hydroxyalkyl, alkoxyl, or the like and Y is nitrile (—C≡N); an amine group of the formula

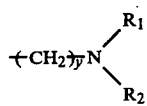

where y is an integer from 0 to 6, and $R_1$ and $R_2$ are hydrogen, alkyl, hydroxyalkyl, aryl, carboalkoxy or carbamyl; or a quaternary amine of the formula

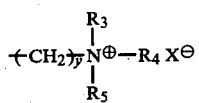

where y is an integer from 0 to 6, $R_3$, $R_4$ and $R_5$ are alkyl, cycloalkyl, aryl or hydroxyalkyl and X is an anion, such as halide, hydroxide, sulfate, nitrate, alkylsulfate, alkylphosphate, fluoroborate and the like.

Various geometric and stereo isomers of the 1,1-disubstituted 2-vinyl- and 2-ethylcyclopropanes, and mixtures and racemates thereof, can be obtained. For example, by varying the process and reaction conditions by which the compounds are prepared it is possible to impart preferential optical activity. Whereas the above formula does not take into account isomeric forms, i.e. cis- and trans-configurations and dextro and levo forms, it is intended that the invention be construed to encompass all such forms and mixtures thereof.

The novel cyclopropane compounds of this invention are obtained using the phase transfer process of U.S. Pat. No. 4,252,739, details of which are incorporated herein by reference. The phase transfer process generally involves reacting an alkylating agent with an activated methylene compound in the presence of an alkali metal compound, water and a quaternary ammonium catalyst. For example, 1-phenyl-1-cyano-2-vinylcyclopropane would be obtained by the reaction of 1,4-dichlorobutene-2, benzyl cyanide and potassium hydroxide in an aqueous system and in the presence of a quaternary ammonium compound, such as tricaprylylmethylammonium chloride. The corresponding 2-ethylcyclopropane compound could then be obtained by reducing the vinyl group with tosyl hydrazine or a similar reducing agent. The reduction is typically carried out in a solvent medium such as diglyme. Cyclopropane compounds having other nitrogen-containing radicals substituted at the 1-position with the phenyl (or other aryl) group are obtained in a similar manner.

As indicated in the formula, one or two groups (R' and R'') can be substituted on the aromatic nucleus. When these groups are hydrocarbon radicals they typically contain from 1 to 20 carbon atoms and, more generally, 1 to 12 carbon atoms. Other common ring substituents can also be present on the aromatic nucleus. Such substituents include alkoxy and hydroxyalkyl groups having from 1 to 12 carbon atoms, halogen (chloro, bromo and fluoro), haloalkyl, nitro, nitrile, amine, thionitrile, mercapto, hydroxy and the like. Especially useful cyclopropane compounds are obtained when R' and R'' are hydrogen, halo, nitro, $C_{1-4}$ alkyl, $C_{3-6}$ cycloalkyl, $C_{6-8}$ aryl, $C_{1-4}$ hydroxyalkyl and $C_{1-4}$ alkoxyl.

The radical Y can be nitrile or a nitrogen-containing radical, such as radicals derived from the nitrile group, including amines, substituted amines, and quaternary amine groups. By hydrogenation of the nitrile group, the corresponding cyclopropyl amine derivative is produced and by further reaction a variety of substituted amines and quaternary amines can be formed. The amine groups will have the formula

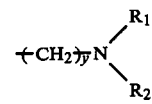

where y is an integer from 0 to 6 and $R_1$ and $R_2$ are hydrogen, alkyl, hydroxyalkyl, aryl, carboalkoxy and carbamyl groups. The alkyl and hydroxyalkyl groups can have from 1 to 8 carbon atoms but more preferably will contain from 1 to 4 carbon atoms. Aryl groups can contain from 6 to 12 carbon atoms. The carboalkoxy groups have the formula

where R* is an alkyl group of from 1 to 8 carbon atoms. Carbamyl groups will have the formula

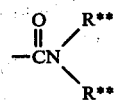

where R** is hydrogen, an alkyl group of from 1 to 8 carbon atoms or an aryl, aralkyl or alkaryl group having from 6 to 12 carbon atoms.

When the amine group is a quaternary amine it will correspond to the formula

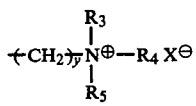

where y is an integer from 0 to 6, $R_3$, $R_4$ and $R_5$ are alkyl, aryl or hydroxyalkyl, and X is an anion such as halide, hydroxide, sulfate, nitrate, alkylsulfate, alkylphosphate, fluoroborate and the like. The alkyl, aryl and hydroxyalkyl groups are the same as defined above for $R_1$ and $R_2$.

In a particularly preferred embodiment of this invention the 2-vinyl- and 2-ethylcyclopropane compounds correspond to the formulae

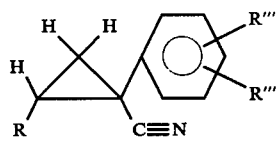

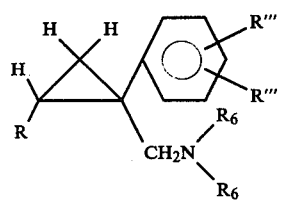

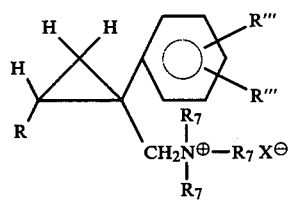

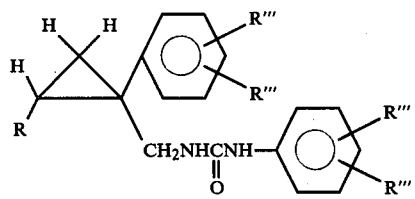

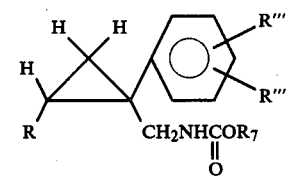

where R and X are the same as defined above, R''' is hydrogen, chloro, bromo, fluoro, nitro, $C_{1-4}$ alkyl, $C_{1-4}$ hydroxyalkyl, $C_{1-4}$ alkoxyl, $R_6$ is hydrogen or a $C_{1-8}$ alkyl and $R_7$ is $C_{1-8}$ alkyl. These compounds and derivatives thereof are particularly useful as herbicides. As employed herein, the term herbicide is used in its broadest sense to encompass any type of modification of plant growth including retardation of growth, defoliation, dessication, regulation, stimulation, dwarfing and, in some cases, killing the plant. In addition to treatment of established plants and emerging seedlings, the compounds of this invention can also be applied as a seed coating.

The compounds of this invention may be used as such or they may be utilized in combination with other known active compounds to enhance the overall herbicidal effectiveness. The ability to develop synergistic herbicidal formulations is generally well recognized and the use of combinations including the products of this invention can provide a means of enhancing the overall activity and/or selectivity of the resulting formulation and/or making the compositions more cost effective. The cyclopropane derivatives may be formulated with an inert carrier or diluent or they may be prepared and utilized in the form of dusts, wettable powders, emulsions and the like.

Additionally, the 1,1-disubstituted 2-vinylcyclopropanes have the ability to polymerize under anionic and radical conditions. These compounds can undergo 1,2-type polymerization via the vinyl group and/or 1,5-type polymerization through a ring-opening mechanism. While these compounds can be homopolymerized, they are most commonly employed in minor amounts with other comonomers.

The following examples illustrate the invention more fully, however, they are not intended as a limitation on the scope thereof. Numerous variations are possible as will be evident to those skilled in the art to which the invention pertains.

EXAMPLE I

1-Cyano-1-phenyl-2-vinylcyclopropane was obtained by the reaction of phenylacetonitrile and 1,4-dichlorobutene-2 in accordance with the process of U.S. Pat. No. 4,252,739. For the reaction, 66 g potassium hydroxide (85%) and 5.69 g triethylbenzylammonium chloride were charged to a glass reactor with 130 cc methylene chloride. A solution of 58.5 g phenylacetonitrile and 68.75 g 1,4-dichlorobutene-2 was then added dropwise to the reaction mixture over a 20 minute period with stirring. The temperature of the reaction was maintained at 25°–30° C. during the addition and subsequent stirring by the application of external cooling. When no further exotherm could be noted (about 3½ hours), 200 cc water was added to the reaction mixture to dissolve salts formed during the reaction. The organic layer was recovered and 97 g crude oil obtained upon evaporation of the methylene chloride. The crude oil was vacuum distilled and 1-cyano-1-phenyl-2-vinylcyclopropane

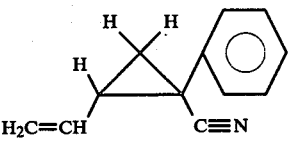

obtained as a yellow oil (boiling point 87° at 0.18 mm Hg) in 53.8% yield. The infrared and nuclear magnetic resonance spectra were consistent with the above structure.

Mass spectrum m/e 169 (M+):

nmr (CDCl₃)τ 2.75 (5 phenyl H, s.); 3.85–5.12 (3 vinyl H, mult.); 7.62–8.08 (1H(2 ring position), mult.); 8.10–8.40(2H(3 ring position), mult.).

The 1-cyano-1-phenyl-2-vinylcyclopropane polymerizes when heated at 95° C. with benzoyl peroxide. Similarly, copolymers are obtained when the 1-cyano-1-phenyl-2-vinylcyclopropane is combined with acrylonitrile and copolymerized.

Similar results are obtained when the above reaction is repeated using substituted-phenylacetonitriles. For example, when 1,4-dichlorobutene-2 is reacted with 6-chloro-2-fluorophenylacetonitrile or 4-nitrophenylacetonitrile in accordance with the above process 1-cyano-1-(6-chloro-2-fluorophenyl)-2-vinylcyclopropane and 1-cyano-1-(4-nitrophenyl)-2-vinylcyclopropane are respectively produced.

EXAMPLE II

A lithium aluminum hydride reduction was carried out on the 1-cyano-1-phenyl-2-vinylcyclopropane obtained from Example I to obtain 1-phenyl-2-vinylcyclopropylcarbinylamine. For the reaction 15.18 g lithium aluminum hydride was dispersed in about 500 cc anhydrous ethyl ether and a solution of 33.5 g 1-cyano-1-phenyl-2-vinylcyclopropane in ethyl ether added dropwise thereto at a rate so that gentle reflux was maintained.

When the addition was complete, the reaction mixture was stirred for six additional hours. Workup of the reaction mixture and evaporation of the ether yielded a colorless liquid which was confirmed to be 1-phenyl-2-vinylcyclopropylcarbinylamine.

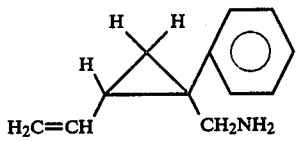

The nuclear magnetic resonance and infrared spectra were consistent with the structure and confirmed disappearance of the nitrile group and the presence of the —NH₂ moiety.

Mass spectrum m/e 173 (M+).

nmr (CDCl₃)τ 2.70 (5 phenyl H, s); 3.85–4.95 (3 vinyl H, mult.); 7.05(2H(—CH₂—N<), s.); 7.85–8.27(3-H(—NH₂, hydrogen 2 ring position), mult.); 8.60–9.17(2H(3 ring position), mult.).

EXAMPLE III

1-Phenyl-2-vinylcyclopropylcarbinylamine was combined with a equimolar amount of phenyl isocyanate in anhydrous ethyl ether and reacted at room temperature with stirring about 16 hours. The ether was then removed under vacuum and the resulting crude material recrystallized from aqueous methanol to obtain 1-(1-phenyl-2-vinylcyclopropylcarbinyl)-3-phenylurea.

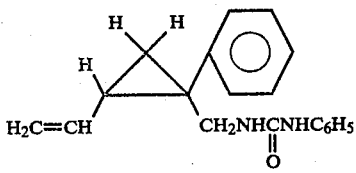

Melting point 130°–132° C.

Mass spectrum m/e 292 (M+).

nmr (CDCl₃)τ 2.60–3.05(10 phenyl H, mult.); 3.27(1H(—NH-CO—), br. mult.); 3.85–5.10(3 vinyl H, mult.); 6.15–6.85(2H(—CH₂—N<), complex mult.); 7.95–8.45(1H(2 cyclopropyl ring position), mult.); 8.55–9.15(2H(3 cyclopropyl ring position), mult.).

EXAMPLE IV

1-Phenyl-2-vinylcyclopropylcarbinylamine was reacted with ethyl chlorodicarbonate and sodium hydroxide to prepare N-(1-phenyl-2-vinylcyclopropylcarbinyl)ethylcarbamate. Essentially equimolar amounts of the reactants were employed. For the reaction, the ethyl chlorodicarbonate and sodium hydroxide were combined in a small amount of ether and 1-Phenyl-2-vinylcyclopropylcarbinylamine added dropwise while maintaining the reaction temperature at 5°–10° C. Reaction was complete after about 1 hour, whereupon the reaction mixture was worked up to obtain N-(1-phenyl-2-vinylcyclopropylcarbinyl)ethylcarbamate.

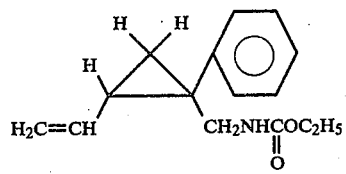

Mass spectrum m/e 245 (M+).

nmr (CDCl₃)τ 2.77(5 phenyl H, s.); 3.85–5.10(3 vinyl H, mult.); 6.02 (2H, q.); 6.20–6.85(2H(—CH₂N<), complex mult.); 7.95–8.45(1H(2 ring position), mult.); 8.60–9.10(2H(3 ring position), mult.); 8.78(3H, tr.); (—NHCO—), hidden.

The N-(1-phenyl-2-vinylcyclopropylcarbinyl)ethylcarbamate was found to inhibit the growth of ryegrass when applied to 7-day old seedlings from a 100 ppm solution. Also, in a senescence test carried out on the leaves of barley, the N-(1-phenyl-2-vinylcyclopropylcarbinyl)ethylcarbamate was found to promote senescence at a 10 ppm level, as determined by measuring the chlorophyll content of the treated leaves.

EXAMPLE V

1-Cyano-1-phenyl-2-ethylcyclopropane was prepared by carrying out a reduction on the corresponding 2-vinylcyclopropane derivative, prepared in accordance with the procedure of Example I, employing tosyl hydrazine. The 1-cyano-1-phenyl-2-vinylcyclopropane (10.14 g) was combined with 22.32 g tosyl hydrazine in 70 cc diglyme and the mixture refluxed with stirring for 1 hour. The reaction mixture was extracted with petroleum ether and, upon distillation, 5.23 g 1-cyano-1-phenyl-2-ethylcyclopropane was obtained. Reduction of the vinyl group was confirmed by the nuclear magnetic resonance spectrum in that there was no absorption at δ5.3. Absence of vinyl absorption was also confirmed by infrared analysis.

Mass spectrum m/e 171 (M+).

nmr (CDCl₃)τ 2.75(5 phenyl H, s.); 7.90–9.25(8H, complex mult.).

Following the procedure of Example II and using the same molar proportions and conditions, the 1-cyano-1-phenyl-2-ethylcyclopropane was then reacted with lithium aluminum hydride to reduce the nitrile group and obtain 1-phenyl-2-ethylcyclopropylcarbinylamine

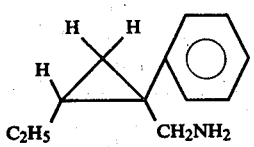

The infrared spectrum was consistent with the above structure as evidenced by the disappearance of absorption for the —C≡N group and the presence of absorption corresponding to the —NH₂ group.

Mass spectrum m/e 175 (M+).

nmr (CDCl₃)τ 2.75(5 phenyl H, s); 7.10, 7.14(2H(—CH₂—N<), s.(cis/trans)); 8.10–9.7(8H, complex mult.).

EXAMPLE VI

From 1-phenyl-2-ethylcyclopropylcarbimylamine, prepared in accordance with the procedure of Example V, N,N-dimethyl-1-phenyl-2-ethylcyclopropylcarbinylamine was obtained using the Eschweiler-Clark methylation procedure. For this reaction, 1-phenyl-2-ethylcyclopropylcarbinylamine is slowly added to a reactor containing about five-fold molar excess formic acid. When the solution clears, about an equal volume of formaldehyde is added and the mixture heated to 90°–100° C. Heating is terminated after 2–3 minutes and resumed when there is no further evaluation of CO₂. The reaction mixture is then heated for about 16 hours at 95°–100° C. About 95% yield crude N,N-dimethyl-1-phenyl-2-ethylcyclopropylcarbinylamine

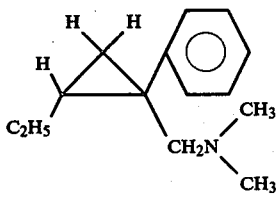

was obtained after workup. The nuclear magnetic resonance spectrum of the purified product was consistent with the desired structure.

Mass spectrum m/e 203 (M+).

nmr (CDCl₃)τ 2.75(5 phenyl H, mult.); 6.92, 7.15(2H(—CH₂—N<), br. s.(cis/trans)); 7.90(6H(—N(CH₃)₂), s.); 8.20–9.70(8H(3 cyclopropane H & —CH₂CH₃), complex mult.).

EXAMPLE VII

A quaternary salt of the N,N-dimethyl-1-phenyl-2-ethylcyclopropylcarbinylamine prepared in Example VI was obtained by reacting the compound with a molar excess of methyl chloride. To obtain the quaternary salt, the N,N-dimethyl-1-phenyl-2-ethylcyclopropylcarbinylamine was charged to a pressure vessel with a small amount of ethanol. The reactor was pressured with methyl chloride and stirred at ambient temperature overnight. Excess methyl chloride was then vented from the reactor, the ethanol evaporated and, after washing with anhydrous ethyl ether and drying under vacuum, (1-Phenyl-2-ethylcyclopropylcarbinyl)-trimethylammonium chloride

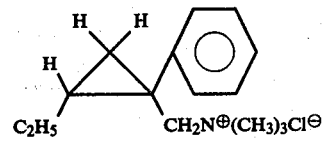

was obtained in good yield as a white soft crystalline deliquescent solid.

nmr (CD₃OD) 2.35–2.95(5 phenyl H, mult.); 5.37, 5.60

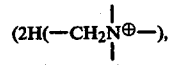

br. s.(cis/trans)); 6.95

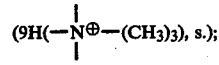

7.95–9.30(8H(cyclopropane H's and (—CH₂CH₃), complex mult.).

When soybean leaves were treated with (1-phenyl-2-ethylcyclopropylcarbinyl)trimethylammonium chloride at a 10 ppm level in a standard test for senescence, the (1-phenyl-2-ethylcyclopropylcarbinyl)trimethylammonium chloride was found to promote senescence, as determined by measuring the chlorophyll content of the treated leaves. Also, when the compound was applied to soybean plants at a 500 ppm level growth retardation was observed.

We claim:

1. A compound of the formula

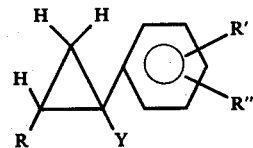

where R is an ethyl or vinyl group, R' and R" are hydrogen, halogen, nitro or a hydrocarbon radical having from 1 to 20 carbon atoms and Y is (a) nitrile;

(b) an amine of the formula

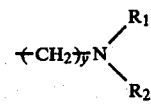

where y is an integer from 0 to 6 and R₁ and R₂ are hydrogen, alkyl, hydroxyalkyl, aryl, carboalkoxy or carbamyl; or (c) a quaternary amine of the formula

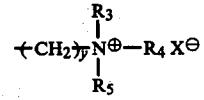

where y is an integer from 0 to 6, $R_3$, $R_4$ and $R_5$ are alkyl, aryl, or hydroxyalkyl and X is halide, hydroxide, sulfate, nitrate, alkylsulfate, alkylphosphate or fluoroborate.

2. A compound according to claim 1 wherein R' and R" are hydrogen, chloro, bromo, fluoro, nitro or an alkyl, aryl, cycloalkyl, alkoxyl or hydroxyalkyl group having from 1 to 12 carbon atoms.

3. A compound according to claim 2 wherein $R_1$ and $R_2$ are $C_{1-8}$ alkyl, $C_{1-8}$ hydroxyalkyl, $C_{6-12}$ aryl, carboalkoxy of the formula

where R* is $C_{1-8}$ alkyl, or carbamyl of the formula

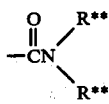

where R** is hydrogen, $C_{1-8}$ alkyl, $C_{1-8}$ aryl, alkaryl or aralkyl, and $R_3$, $R_4$ and $R_5$ are $C_{1-8}$ alkyl, $C_{1-8}$ hydroxyalkyl or $C_{6-12}$ aryl.

4. A compound of the formula

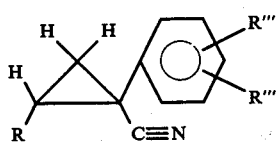

where R is ethyl or vinyl and R''' is hydrogen, chloro, bromo, fluoro, nitro, $C_{1-4}$ alkyl, $C_{1-4}$ hydroxyalkyl or $C_{1-4}$ alkoxyl.

5. A compound of the formula

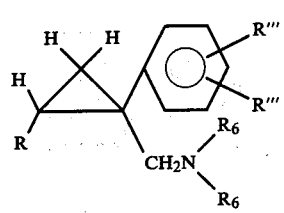

where R is ethyl or vinyl, R''' is hydrogen, chloro, bromo, fluoro, nitro, $C_{1-4}$ alkyl, $C_{1-4}$ hydroxyalkyl or $C_{1-4}$ alkoxyl, and $R_6$ is hydrogen or $C_{1-8}$ alkyl.

6. A compound of the formula

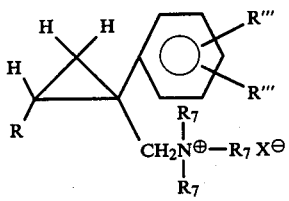

where R is ethyl or vinyl, R''' is hydrogen, chloro, bromo, fluoro, nitro, $C_{1-4}$ alkyl, $C_{1-4}$ hydroxyalkyl or $C_{1-4}$ alkoxyl, $R_7$ is $C_{1-8}$ alkyl, and X is halide, hydroxide, sulfate, nitrate, alkylsulfate, alkylphosphate or fluoroborate.

7. A compound of the formula

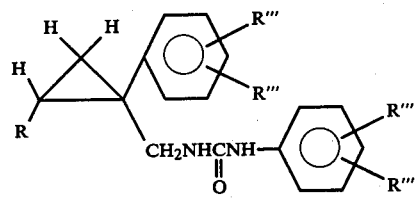

where R is ethyl or vinyl and R''' is hydrogen, chloro, bromo, fluoro, nitro, $C_{1-4}$ alkyl, $C_{1-4}$ hydroxyalkyl or $C_{1-4}$ alkoxyl.

8. A compound of the formula

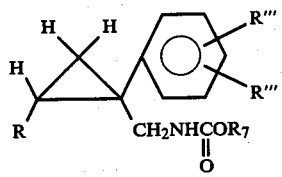

where R is ethyl or vinyl, R''' is hydrogen, chloro, bromo, fluoro, nitro, $C_{1-4}$ alkyl, $C_{1-4}$ hydroxyalkyl or $C_{1-4}$ alkoxyl, and $R_7$ is a $C_{1-8}$ alkyl.

* * * * *